United States Patent
Ando et al.

(10) Patent No.: US 12,220,395 B2
(45) Date of Patent: Feb. 11, 2025

(54) INTERMITTENT ENDURANCE CAPACITY IMPROVING AGENT OR BLOOD PH ELEVATING AGENT

(71) Applicant: AJINOMOTO CO., INC., Tokyo (JP)

(72) Inventors: Tomoko Ando, Kawasaki (JP); Sakiko Toyoda, Kawasaki (JP); Hiroyuki Kato, Kawasaki (JP); Yoshihito Nogusa, Tokyo (JP)

(73) Assignee: AJINOMOTO CO., INC., Tokyo (JP)

( * ) Notice: Subject to any disclaimer, the term of this patent is extended or adjusted under 35 U.S.C. 154(b) by 877 days.

(21) Appl. No.: 17/182,794

(22) Filed: Feb. 23, 2021

(65) Prior Publication Data
US 2021/0177793 A1 Jun. 17, 2021

Related U.S. Application Data (63) Continuation of application No. PCT/JP2019/034061, filed on Aug. 30, 2019.

(30) Foreign Application Priority Data

Aug. 31, 2018 (JP) .................... 2018-162594

(51) Int. Cl.
| | |
|---|---|
| *A61K 31/198* | (2006.01) |
| *A23L 33/00* | (2016.01) |
| *A23L 33/175* | (2016.01) |
| *A61K 9/00* | (2006.01) |
| *A61P 21/00* | (2006.01) |

(52) U.S. Cl.
CPC .......... *A61K 31/198* (2013.01); *A23L 33/175* (2016.08); *A23L 33/40* (2016.08); *A61K 9/0053* (2013.01); *A61P 21/00* (2018.01); *A23V 2002/00* (2013.01)

(58) Field of Classification Search
CPC ... A61K 31/198; A61K 9/0053; A23L 33/175; A23L 33/40; A23L 33/30; A23V 2002/00; A61P 3/00; A61P 3/02; A61P 19/06; A61P 43/00
See application file for complete search history.

(56) References Cited

U.S. PATENT DOCUMENTS

| | | |
|---|---|---|
| 2006/0003083 A1 | 1/2006 | Kouda et al. |
| 2010/0144815 A1 | 6/2010 | Tsuchita et al. |
| 2010/0267794 A1 | 10/2010 | Saito et al. |

FOREIGN PATENT DOCUMENTS

| | | |
|---|---|---|
| JP | 2009-159984 A | 7/2009 |
| JP | 4913410 B2 | 4/2012 |
| JP | 5775668 B2 | 9/2015 |
| JP | 2017-88549 A | 5/2017 |

(Continued)

OTHER PUBLICATIONS

Baguet, A. et al. Beta-alanine supplementation reduces acidosis but not oxygen uptake response during high-intensity cycling exercise. Eur. J. Appl. Physiol. 2010, 108 (3), pp. 495-503, abstract, etc.*

(Continued)

*Primary Examiner* — Deborah D Carr
(74) *Attorney, Agent, or Firm* — Oblon, McClelland, Maier & Neustadt, L.L.P.

(57) ABSTRACT

Agents containing either or both of aspartic acid and tyrosine are effective for improving intermittent endurance capacity.

7 Claims, 3 Drawing Sheets

* p<0.05, * P<0.001, ** p<0.0001, Dunnett's multiple comparison test. (vs DW)

(56) References Cited

FOREIGN PATENT DOCUMENTS

| JP | 2018-24619 A | 2/2018 | | |
|---|---|---|---|---|
| WO | WO-2008105368 A1 | * | 9/2008 | ............... A23L 2/52 |
| WO | WO-2010041647 A1 | * | 4/2010 | ............... A23L 2/52 |

OTHER PUBLICATIONS

Tamaki, Nanaya,Research on Biosynthetic Pathways of Anserine and Carmnosine, Summary of Thesis of Osaka University, ,pp. 374-377 (concise English transiation), 1971.*
Saunders, B. et al. Beta-alanine supplementation improves YoYo intermittent recovery test performance. J. Int. Soc. Sports Nutr. 2012, 9 ( 1), 39, abstract, "Introduction" on pp. 1-2, fig. 1, etc.*
Furst, T. et al. Beta-Alanine supplementation increased physical performance and improved executive function following endurance exercise in middle aged individuals. J. Int. Soc. Sports Nutr. Jul. 2018, 15 (1), 32, abstract, etc.*
Santana, J. O. et al. Beta-Alanine Supplementation Improved 10-km Running Time Trial in Physically Active Adults. Front. Physiol. Aug. 8, 2018, vol. 9, article 1105, abstract, etc.*
Culbertson, J. Y. et al. Effects of Beta-alanine on muscle carnosine and exercise performance: a review of the current literature . Nutrients. 2010, 2{1), pp. 75-98, abstract, table 1, etc.*
International Search Report and Written Opinion issued Nov. 26, 2019 in PCT/JP2019/034081 (submitting English translation only), 14 pages.
Bryan Saunders, et al., "ß-alanine supplementation improves YoYo intermittent recovery test performance", Journal of the International Society of Sports Nutrition, (2012), 5 pages.

Tamaki, Nanaya, "Research on Biosynthetic Pathways of Anserine and Carnosine", Summary of Thesis of Osaka University, http://hdl.handle.net/11094/27719, (1971), pp. 374-377 (concise English translation found in Written Opinion of ISR PCT/JP2019/034061).
Taylor Furst, et al., "ß-Alanine supplementation increased physical performance and improved executive function following endurance exercise in middle aged individuals", Journal of the International Society of Sports Nutrition, (2018), 8 pages.
Jeferson O. Santana, et al., "Beta-Alanine Supplementation Improved 10-km Running Time Trial in Physically Active Adults", Frontiers in Physiology, (2018), 6 pages.
Julie Y. Culbertson, et al., "Effects of Beta-Alanine on Muscle Carnosine and Exercise Performance: A Review of the Current Literature", Nutrients, (2010), pp. 75-97.
Audrey Baguet, et al . . . "ß-Alanine supplementation reduces acidosis but not oxygen uptake response during high-intensity cycling exercise", European Journal of Applied Physiology, vol. 108. (2010), pp. 495-503.
Nicole A. Coull, et al., "Effect of tyrosine ingestion on cognitive and physical performance utilising an intermittent soccer performance test (ISPT) in a warm environment", European Journal of Applied Physiology, vol. 115, (2015), pp. 373-386.
Magni Mohr, et al., "Caffeine intake improves intense intermittent exercise performance and reduces muscle interstitial potassium accumulation", Journal of Applied Physiology, vol. 111, (2011), pp. 1372-1379.
Omori, O.K., et al., "Relationship between intermittent endurance performance and whole body endurance in college soccer players", Tairyoku Kagaku, Faculty of Human and Cultural Studies, University of East Asia, 2004, vol. 53, No. 6, p. 810, 356 (with English translation).

* cited by examiner

INTERMITTENT ENDURANCE CAPACITY IMPROVING AGENT OR BLOOD PH ELEVATING AGENT

CROSS REFERENCE TO RELATED APPLICATIONS

This application is a continuation of International Patent Application No. PCT/JP2019/034061, filed on Aug. 30, 2019, and claims priority to Japanese Patent Application No. 2018-162594, filed on Aug. 31, 2018, both of which are incorporated herein by reference in their entireties.

BACKGROUND OF THE INVENTION

Field of the Invention

The present invention relates to intermittent endurance capacity improving agents and the like. The present invention further relates to methods for improving intermittent endurance capacity with such an agent. The present invention also relates to blood pH increasing agents and the like. The present invention further relates to methods for increasing blood pH with such an agent.

Discussion of the Background

In sport science, the capacity for endurance is largely divided into "whole body endurance capacity" and "intermittent endurance capacity". The "whole body endurance capacity" is also called aerobic endurance capacity or continuous endurance capacity, and refers to an ability to continue exercising at a constant intensity for a long time. The sports where the whole body endurance capacity is important include marathon and the like.

On the other hand, "intermittent endurance capacity" refers to an ability to repeatedly continue high-intensity exercise while performing low- and medium-intensity exercises and rest in between. The sports where the intermittent endurance capacity is important include game sports such as soccer, basketball and the like.

Basically, to increase "whole body endurance capacity", it is preferable to perform exercises that require whole body endurance capacity (e.g., long-distance running and the like). On the other hand, to increase "intermittent endurance capacity", it is preferable to perform exercises that require intermittent endurance capacity (e.g., interval training and the like). Therefore, it is considered that the "whole body endurance capacity" and the "intermittent endurance capacity" are based on different physiological action/action mechanism.

Compositions for improving whole body endurance capacity have been reported to date. For example, WO 2010/041647, which is incorporated herein by reference in its entirety, discloses an endurance capacity improving agent containing amino acid as the main component. JP-A-2018-024619, which is incorporated herein by reference in its entirety, discloses an endurance capacity improving agent containing a branched α-glucan mixture as the main component. Furthermore, JP-A-2017-088549, which is incorporated herein by reference in its entirety, discloses an endurance capacity improving agent containing S-allylcysteine as the active ingredient.

However, all these endurance capacity improving agents aim at improving whole body endurance capacity and do not aim at improving intermittent endurance capacity.

Amino acids are components abundant in general food and drink, and they are not doping components. There are many reports on the use of amino acids as nutrition aid foods during exercise and pharmaceutical products. For example, as shown in the aforementioned WO 2010/041647, which is incorporated herein by reference in its entirety, it is widely known that ingestion of specific amino acids can improve exercise function. For example, it is known that BCAA (branched chain amino acid: valine, leucine, and isoleucine) is effective in preventing decomposition of muscle protein due to exercise and preventing fatigue (see JP-B-5775668, which is incorporated herein by reference in its entirety). Also, it has been reported that, as a pharmaceutical product, glycine intake can induce deeper sleep (see JP-B-4913410, which is incorporated herein by reference in its entirety). Therefore, it is considered highly beneficial to elucidate the action of a wide variety of amino acids on living organisms and apply the amino acids.

Aspartic acid, which is one of the non-essential amino acids, is known to be involved in both the TCA cycle and the ornithine cycle in vivo, and is one of the important amino acids. It is known that aspartic acid is generally known to have a fatigue recovery effect and the like by promoting the decomposition of lactic acid, which is a fatigue substance.

SUMMARY OF THE INVENTION

The endurance capacity improving agents described in WO 2010/041647; JP-A-2018-024619; and JP-A-2017-088549, all of which are incorporated herein by reference in their entireties, may be, as described above, useful in sports mainly requiring whole body endurance capacity such as marathon and the like. When intermittent endurance capacity is required, such endurance capacity improving agents cannot afford a sufficient effect.

Therefore, it is one object of the present invention to provide novel means of improving intermittent endurance capacity.

It is another object of the present invention to provide novel applications of amino acid by specifying an unidentified action mechanism involving amino acid.

It is another object of the present invention to provide novel methods of improving intermittent endurance capacity.

It is another object of the present invention to provide novel methods of increasing blood pH.

These and other objects, which will become apparent during the following detailed description, have been achieved by the inventors' discovery that aspartic acid or tyrosine has an effect of improving intermittent endurance capacity. The present inventors have also found that a very high intermittent endurance capacity improving effect can be obtained by using aspartic acid and tyrosine in combination, particularly, by using these in combination at a specific mixing ratio.

In addition to these, the present inventors have found that the blood pH in the subject is efficiently elevated when aspartic acid improves intermittent endurance capacity.

That is, the present invention provides the following:
(1) An intermittent endurance capacity improving agent comprising either or both of aspartic acid and tyrosine.
(2) The agent of (1), wherein the agent comprises aspartic acid and tyrosine.
(3) The agent of (2), wherein a ratio of aspartic acid to tyrosine is aspartic acid:tyrosine=1:0.1 to 10 in weight ratio.
(4) A blood pH increasing agent comprising aspartic acid.

(5) The agent of (4), wherein the agent is used for improving acidosis.
(6) The agent of (4) or (5), wherein the agent is used for the treatment, improvement, or prophylaxis of one or more diseases selected from the group consisting of the following:
  (1) hyperuricemia
  (2) gout.
(7) A food or drink comprising the agent of any of (1) to (6).
(A-1) Use of a composition comprising either or both of aspartic acid and tyrosine in producing a medicament for improving intermittent endurance capacity.
(A-2) The use of (A-1), wherein the composition comprises aspartic acid and tyrosine.
(A-3) The use of (A-2), wherein the ratio of aspartic acid to tyrosine in the composition is aspartic acid:tyrosine=1:0.1 to 10 in weight ratio.
(A-4) Use of a composition comprising aspartic acid in producing a medicament for increasing blood pH.
(A-5) The use of (A-4), wherein the medicament for increasing blood pH is a medicament for improving acidosis.
(A-6) The use of (A-4) or (A-5), wherein the medicament for increasing blood pH is a medicament for the treatment, improvement, or prophylaxis of one or more diseases selected from the group consisting of the following:
  (1) hyperuricemia
  (2) gout.
(A-7) The use of any of (A-1) to (A-6), wherein the composition is a food or drink.
(B-1) A composition comprising either or both of aspartic acid and tyrosine for use in improving intermittent endurance capacity.
(B-2) The composition of (B-1), comprising aspartic acid and tyrosine.
(B-3) The composition of (B-2), wherein the ratio of aspartic acid to tyrosine is aspartic acid:tyrosine=1:0.1 to 10 in weight ratio.
(B-4) A composition containing aspartic acid for use in increasing blood pH.
(B-5) The composition of (B-4) for improving acidosis.
(B-6) The composition of (B-4) or (B-5) for use for the treatment, improvement, or prophylaxis of one or more diseases selected from the group consisting of the following:
  (1) hyperuricemia
  (2) gout.
(B-7) The composition of any of (B-1) to (B-6), wherein the composition is a food or drink.
(C-1) A method for improving intermittent endurance capacity in a subject, including administering an effective amount of either or both of aspartic acid and tyrosine to the subject.
(C-2) The method of (C-1), wherein the subject is administered with effective amounts of aspartic acid and tyrosine.
(C-3) The method of (C-2), wherein the ratio of aspartic acid to tyrosine is aspartic acid:tyrosine=1:0.1 to 10 in weight ratio.
(C-4) A method for increasing blood pH of a subject, including administering an effective amount of aspartic acid to the subject.
(C-5) The method of (C-4) for improving acidosis of a subject.
(C-6) The method of (C-4) or (C-5) for the treatment, improvement, or prophylaxis of one or more diseases selected from the group consisting of the following:
  (1) hyperuricemia
  (2) gout.
(C-7) The method of any of (C-1) to (C-6), wherein either or both of aspartic acid and tyrosine is/are contained in a food or drink.
(D-1) Use of a composition comprising either or both of aspartic acid and tyrosine for use in improving intermittent endurance capacity.
(D-2) The use of (D-1), wherein the composition comprising aspartic acid and tyrosine.
(D-3) The use of (D-2), wherein the ratio of aspartic acid to tyrosine in the composition is aspartic acid:tyrosine=1:0.1 to 10 in weight ratio.
(D-4) Use of a composition comprising aspartic acid in increasing blood pH.
(D-5) The use of (D-4), wherein the blood pH is increased to improve acidosis.
(D-6) The use of any of (D-1) to (D-5), wherein the composition is a food or drink.

Advantageous Effects of Invention

According to the present invention, intermittent endurance capacity of a subject can be improved. In another embodiment of the present invention, blood pH of a subject can also be increased safely and efficiently.

DETAILED DESCRIPTION OF THE PREFERRED EMBODIMENTS

The present invention is described in detail in the following.

In the present specification, the "intermittent endurance capacity" refers to an ability to repeatedly continue high-intensity exercise (e.g., dash, etc.) while performing low- or medium-intensity exercise (e.g., jog, etc.) and/or rest in between. The intermittent endurance capacity is resistance (endurance) to exercise repeatedly performing high-intensity anaerobic exercise and low-intensity aerobic exercise (intermittent exercise). It is a concept different from the whole body endurance capacity (or continuous endurance capacity) which means resistance to exercise continuously performing low- or middle-intensity aerobic exercise (continuous exercise). The present invention can improve intermittent endurance capacity, and the improvement in the intermittent endurance capacity can be evaluated by a method known per se. For example, it can be evaluated using the YO-YO intermittent endurance test (Intermittent endurance-Test) described in detail in the following Example.

1. Intermittent Endurance Capacity Improving Agent

The present invention provides an intermittent endurance capacity improving agent containing either or both of aspartic acid and tyrosine (hereinafter sometimes referred to as "the intermittent endurance capacity improving agent of the present invention").

As the aspartic acid and tyrosine to be mixed in the intermittent endurance capacity improving agent of the present invention, any of L-form, D-form and DL-form can be used. It is preferably L-form or DL-form, further preferably L-form. In the present specification, the terms "aspartic acid" and "tyrosine" mean a concept encompassing not only free forms but also salt forms thereof. The salts of aspartic acid and tyrosine specifically include salts with inorganic base, organic base, inorganic acid, organic acid and salts with amino acid and the like.

Specific examples of the salt with inorganic base include salts with alkali metals such as lithium, sodium, potassium and the like, salts with alkaline earth metals such as magnesium, calcium and the like, ammonium salt and the like. Examples of the salt with organic base include salts with alkanol amines such as monoethanolamine, diethanolamine, triethanolamine and the like, salts with heterocyclic amines such as morpholine, piperidine and the like, and the like. Examples of the salts with inorganic acids include salts with hydrohalic acid (hydrochloric acid, hydrobromic acid, hydroiodic acid etc.), sulfuric acid, nitric acid, phosphoric acid and the like. Examples of the salt with organic acid include salts with monocarboxylic acids such as formic acid, acetic acid, propanoic acid and the like; salts with saturated dicarboxylic acids such as oxalic acid, malonic acid, malic acid, succinic acid and the like; salts with unsaturated dicarboxylic acids such as maleic acid, fumaric acid and the like; salts with tricarboxylic acids such as citric acid and the like; and salts with keto acids such as α-ketoglutaric acid and the like, and the like. Examples of the salt with amino acid include salts with aliphatic amino acids such as glycine, alanine and the like; salts with aromatic amino acids such as phenylalanine and the like; salts with basic amino acids such as lysine and the like; salts with acidic amino acid such as glutamic acid and the like; salts with amino acids that form lactam such as pyroglutamic acid and the like, and the like. From the viewpoint of easy availability and easy handling, aspartic acid is preferably a sodium salt and tyrosine is preferably a free form.

In the present invention, aspartic acid and tyrosine, and a salt thereof to be used may be extracted from animals, plants or the like, which are naturally present, and purified, or obtained by a chemical synthesis method, a fermentation method, an enzyme method or a gene recombinant method. Commercially available products provided by various companies may also be used.

The amount of aspartic acid or tyrosine in the intermittent endurance capacity improving agent of the present invention is generally 0.01 wt % to 99.9 wt %, preferably 0.1 wt % to 99.9 wt %, more preferably 10 wt % to 99.9 wt %, further preferably 30 wt % to 99.9 wt %, particularly preferably 40 wt % to 99.9 wt %, based on the total weight of the agent. In one embodiment, when the intermittent endurance capacity improving agent of the present invention is in a granular form, the amount of aspartic acid or tyrosine in the intermittent endurance capacity improving agent of the present invention may be generally 10 wt % to 99.9 wt %, preferably 30 wt % to 99.9 wt %, more preferably 40 wt % to 99.9 wt %, further preferably 50 wt % to 90 wt %, particularly preferably 55 wt % to 85 wt %, based on the total weight of the agent. In one embodiment, when the intermittent endurance capacity improving agent of the present invention is in a jelly form, the amount of aspartic acid or tyrosine in the intermittent endurance capacity improving agent of the present invention may be generally 0.01 wt % to 50 wt %, preferably 0.1 wt % to 30 wt %, more preferably 1 wt % to 20 wt %, further preferably 1 wt % to 15 wt %, particularly preferably 1.5 wt % to 15 wt %, based on the total weight of the agent. In one embodiment, when the intermittent endurance capacity improving agent of the present invention is in a liquid form, the amount of aspartic acid or tyrosine in the intermittent endurance capacity improving agent of the present invention may be generally 0.01 wt % to 10 wt %, preferably 0.01 wt % to 5 wt %, more preferably 0.05 wt % to 5 wt %, further preferably 0.08 wt % to 2.5 wt %, particularly preferably 0.1 wt % to 1.5 wt %, based on the total weight of the agent. When the both components of aspartic acid and tyrosine are used in combination, the sum of the weights of the both components may be included in such ranges. When aspartic acid and tyrosine mixed in the intermittent endurance capacity improving agent of the present invention are in salt forms, the amounts thereof converted to free form is included in the above-mentioned ranges.

In one preferable embodiment, aspartic acid and tyrosine are mixed with the intermittent endurance capacity improving agent of the present invention. When aspartic acid and tyrosine are mixed, a higher intermittent endurance capacity improving effect can be obtained by setting the mixing ratio of aspartic acid and tyrosine to generally aspartic acid:tyrosine=1:0.1 to 10, preferably aspartic acid:tyrosine=1:0.2 to 5, more preferably aspartic acid:tyrosine=1:0.3 to 3, further preferably aspartic acid:tyrosine=1:0.5 to 2, particularly preferably aspartic acid:tyrosine=1:0.8 to 1.2, in the weight ratio. When aspartic acid and tyrosine mixed with the intermittent endurance capacity improving agent of the present invention are in salt forms, the mixing ratio thereof converted to free form is included in the above-mentioned ranges.

When the intermittent endurance capacity improving agent of the present invention is provided in a unit package form per single intake amount, it can be provided, for example, in the following amounts. When aspartic acid (or a salt thereof) alone is mixed as the active ingredient, 0.1 to 6 g (preferably, 0.5 to 5 g, more preferably 1 to 5 g, further preferably 2 to 5 g, particularly preferably 3 to 5 g) thereof is mixed per single intake amount converted to aspartic acid amount. When aspartic acid (or a salt thereof) and tyrosine (or a salt thereof) are contained as the active ingredients, 0.1 to 3 g of aspartic acid and 0.1 to 3 g of tyrosine (preferably, 0.5 to 3 g of aspartic acid and 0.5 to 3 g of tyrosine, more preferably 1 to 3 g of aspartic acid and 1 to 3 g of tyrosine, particularly preferably 1.5 to 2.5 g of aspartic acid and 1.5 to 2.5 g of tyrosine) are mixed per single intake amount converted to aspartic acid amount and tyrosine amount.

In the present specification, an agent consisting of the "unit package form per single intake amount" is an agent in a form with a pre-determined amount to be taken per single ingestion. Examples of the unit package form per single intake amount include a form that defines a given amount in a pack, package, bottle, etc. In the case of granular, powdery, tablet, and slurry agents, a form such as package, and the like that defines a given amount, and a form such as a container and the like that indicates the intake amount per single ingestion can be mentioned.

The intermittent endurance capacity improving agent of the present invention may contain further components as long as the characteristics of the present invention are not impaired. As such component, amino acids other than aspartic acid and/or tyrosine (e.g., BCAA, alanine, proline, glycine etc.) or a salt thereof, sweeteners (e.g., aspartame, acesulfame potassium, licorice extract, etc.), carbohydrates (e.g., maltodextrin, palatinose, etc.), sodium bicarbonate, sodium citrate, and the like may be contained as appropriate.

The intermittent endurance capacity improving agent of the present invention can be ingested by a subject by a general administration route, such as oral administration, administration into blood, rectal administration and the like, and oral administration (oral ingestion) is preferable. The timing of the administration (ingestion) of the intermittent endurance capacity improving agent of the present invention is not particularly limited as long as a desired effect is obtained, and it is generally preferably before or during performing intermittent exercise. When it is before performing intermittent exercise, it can be unlimitatively administered to (ingested by) the subject immediately before to 3 hr before, preferably, immediately before to 2 hr before, particularly preferably, immediately before to 1 hr before, performing intermittent exercise.

The dose (intake amount) of the intermittent endurance capacity improving agent of the present invention is not particularly limited as long as a desired effect can be obtained. It can be appropriately set in consideration of the age, body weight, health condition and the like of the subject, and the total intake amount of aspartic acid and/or tyrosine is, for example, generally 0.01 to 0.2 g/kg of body weight, preferably 0.02 to 0.2 g/kg of body weight, particularly preferably 0.1 to 0.2 g/kg of body weight.

The intermittent endurance capacity improving agent of the present invention can be in a solid form such as powder, granule, tablet, and the like, or in a form such as semi-solid, jelly, slurry, liquid and the like; however, the form is not limited thereto.

The intermittent endurance capacity improving agent of the present invention can be used for a therapeutic or non-therapeutic object. For therapeutic use, the intermittent endurance capacity improving agent of the present invention is applied to a subject affected with a disease accompanying a decrease in the intermittent endurance capacity. For non-therapeutic use, the intermittent endurance capacity improving agent of the present invention is applied to a healthy subject.

2. Blood pH Increasing Agent

The present invention also provides a blood pH increasing agent containing aspartic acid (hereinafter sometimes referred to as "the blood pH increasing agent of the present invention").

As the aspartic acid to be mixed with the blood pH increasing agent of the present invention, any of L-form, D-form and DL-form can be used. It is preferably L-form or DL-form, further preferably L-form. The aspartic acid may be in a salt form as mentioned above.

The amount of aspartic acid used in the blood pH increasing agent of the present invention is generally 0.01 wt % to 99.9 wt %, preferably 0.1 wt % to 99.9 wt %, more preferably 10 wt % to 99.9 wt %, further preferably 30 wt % to 99.9 wt %, particularly preferably 50 wt % to 99.9 wt %, based on the total weight of the agent. In one embodiment, when the blood pH increasing agent of the present invention is in a granular form, the amount of aspartic acid used in the blood pH increasing agent of the present invention may be generally 10 wt % to 99.9 wt %, preferably 30 wt % to 99.9 wt %, more preferably 40 wt % to 99.9 wt %, further preferably 50 wt % to 90 wt %, particularly preferably 55 wt % to 85 wt %, based on the total weight of the agent. In one embodiment, when the intermittent endurance capacity improving agent of the present invention is in a jelly form, the amount of aspartic acid or tyrosine in the intermittent endurance capacity improving agent of the present invention may be generally 0.01 wt % to 50 wt %, preferably 0.1 wt % to 30 wt %, more preferably 1 wt % to 20 wt %, further preferably 1 wt % to 15 wt %, particularly preferably 1.5 wt % to 15 wt %, based on the total weight of the agent. In one embodiment, when the blood pH increasing agent of the present invention is in a liquid form, the amount of aspartic acid used in the blood pH increasing agent of the present invention may be generally 0.01 wt % to 10 wt %, preferably 0.01 wt % to 5 wt %, more preferably 0.05 wt % to 5 wt %, further preferably 0.08 wt % to 2.5 wt %, particularly preferably 0.1 wt % to 1.5 wt %, based on the total weight of the agent. When aspartic acid used in the blood pH increasing agent of the present invention is in a salt form, the amount thereof converted to free form is included in the above-mentioned ranges.

When the blood pH increasing agent of the present invention is provided in a unit package form per single intake amount, for example, it can be provided in a form containing the aspartic acid to be the active ingredient in the following amount: 0.1 to 6 g (preferably 0.5 to 5 g, more preferably 1 to 5 g, further preferably 2 to 5 g, particularly preferably 3 to 5 g), per single ingestion when converted to aspartic acid amount.

The blood pH increasing agent of the present invention shows an effect of increasing the blood pH of a subject when administered to or ingested by the subject. Ingestion of the blood pH increasing agent of the present invention can suppress a decrease in blood pH due to high-intensity exercise. Thus, muscle contraction can be repeated at a higher level.

In one embodiment, the blood pH increasing agent of the present invention can also be used for the treatment and/or mitigation of a disease or a physiological state associated with low pH in the blood. As shown in the following Example, the blood pH increasing agent of the present invention shows a higher pH increasing effect than sodium hydrogen carbonate used as an existing blood pH increasing agent. Therefore, it is considered that the blood pH increasing agent of the present invention can be preferably used instead of sodium hydrogen carbonate and/or sodium citrate (or citric acid potassium) for conditions and diseases to which sodium hydrogen carbonate and sodium citrate (or citric acid potassium) can be applied as a therapeutic agent, an improving agent and/or a prophylactic agent. In consideration of such aspect, the conditions and diseases to which the blood pH increasing agent of the present invention can be applied include "acidosis", "hyperuricemia", "gout" and the like.

Acidosis (also referred to as "acidemia" or the like) refers to a state in which acid is abnormally accumulated or bases are lost in body fluids due to various reasons. The pH of normal mammalian (especially human) body fluids is maintained in the range of 7.35 to 7.45 mainly by the action of the carbonic acid buffer system based on the equilibrium of carbonic acid (acidic) and bicarbonic acid (alkaline). In the state determined to be acidosis, the hematological pH becomes not more than 7.35 for some reason. What causes acidosis includes, but is not limited to, intense exercise, temporary hypoxia due to lung disease, malnutrition and the like. Acidosis is roughly divided into metabolic acidosis and respiratory acidosis. Metabolic acidosis occurs when large amounts of acidic metabolites are present due to a decrease in the processing capacity of the liver, or conversely as a result of overproduction, which not only lowers the pH but also reduces carbon dioxide in the blood. On the other hand, respiratory acidosis occurs when carbon dioxide and the like cannot be excreted sufficiently from the lung and kidney, in which pH is low but the amount of carbon dioxide in the blood is higher than normal. In one embodiment of the present invention, acidosis may be metabolic or respiratory acidosis. In another embodiment of the present invention, acidosis may be ketoacidosis (e.g., including, but not limited to, diabetic ketoacidosis (DKA), alcoholic ketoacidosis, ketoacidosis caused by malnutrition, and the like).

As described in detail in the following Example, the blood pH increasing agent of the present invention has a blood pH increasing effect superior to that of sodium hydrogen carbonate. Therefore, in one embodiment, the blood pH increasing agent of the present invention is considered to be preferably applicable to diseases to which sodium hydrogen carbonate and sodium citrate (or citric acid potassium) can be applied as a therapeutic agent, an improving agent, and/or a prophylactic agent. Examples of the disease include "hyperuricemia" and "gout". As used herein, "hyperuricemia" refers to a state in which uric acid in the blood increases abnormally due to increased uric acid synthesis and decreased excretion of uric acid in the kidney, and the serum uric acid level exceeds 7.0 milligram per deciliter. It has been reported that hyperuricemia left untreated increases the risk of developing gout. "Gout" is a disease based on hyperuricemia in which the uric acid level in the blood becomes abnormally high, and shows crystallized uric acid accumulated in the toe joint, resulting in severe pain.

Examples of the subject to which the blood pH increasing agent of the present invention can be applied include mammals (e.g., human, monkey, mouse, rat, guinea pig, hamster, rabbit, cat, dog, bovine, horse, donkey, swine, sheep etc.), preferably human.

The blood pH increasing agent of the present invention can be formulated into various forms such as liquid; semi-solid; solid (e.g., powder, granule, tablet, capsule and the like), and the like by adding other nutrition components, pharmaceutically acceptable additives, and the like besides aspartic acid and by using a formulation means well known in the field of preparations.

The above-mentioned pharmaceutically acceptable additive can be appropriately selected according to the form of the blood pH increasing agent of the present invention and, for example, excipient, binder, disintegrant, lubricant, coating agent, base, solvent, solubilizing agents, solubilizer, emulsifier, dispersing agent, suspending agent, stabilizer, thickener, soothing agent, isotonicity agent, antioxidant, antiseptic, preservative, corrigent, sweetener, flavor, colorant and the like can be mentioned.

To be specific, examples of the excipient include magnesium carbonate, saccharides (glucose, lactose, cornstarch etc.), sugar alcohol (sorbitol, mannitol etc.) and the like. Examples of the binder include gelatin, pregelatinized starch, partly pregelatinized starch, cellulose and a derivative thereof (crystalline cellulose, hydroxypropylcellulose etc.) and the like.

Examples of the disintegrant include crospovidone, povidone, crystalline cellulose and the like. Examples of the lubricant include talc, magnesium stearate and the like. Examples of the coating agent include methacrylic acid-methyl methacrylate copolymer, methacrylic acid-ethyl acrylate copolymer, methyl methacrylate-butyl methacrylate-dimethylaminoethyl methacrylate copolymer, ethyl acrylate-methyl methacrylate-trimethylammonioethylmethacrylate chloride copolymer and the like.

Examples of the base include animal and plant fats and oils (olive oil, cacao butter, beef tallow, sesame oil, hydrogenated oil, castor oil etc.), wax (Carnauba wax, beeswax etc.), polyethylene glycol and the like. Examples of the solvent include purified water, water for injection, monovalent alcohol (ethanol etc.), polyhydric alcohol (glycerol etc.) and the like. Examples of the solubilizing agent include propylene glycol, medium-chain triglyceride and the like.

Examples of the solubilizer, emulsifier, dispersing agent and suspending agent include surfactant and the like such as sorbitan fatty acid ester, glycerol fatty acid ester, polyoxyethylene sorbitan fatty acid ester (polysorbate 20, polysorbate 80 etc.), polyoxyethylene hydrogenated castor oil, sucrose fatty acid ester and the like.

Examples of the stabilizer include adipic acid, β-cyclodextrin, ethylenediamine, sodium edetate and the like. Examples of the thickener include water-soluble polymer (sodium polyacrylate, carboxyvinyl polymer etc.), polysaccharides (sodium alginate, xanthan gum, tragacanth etc.) and the like. Examples of the soothing agent include ethyl aminobenzoate, chlorobutanol, propylene glycol, benzyl alcohol and the like. Examples of the isotonicity agent include potassium chloride, sodium chloride, sorbitol, saline and the like. Examples of the pH adjuster include hydrochloric acid, sulfuric acid, acetic acid, citric acid, lactic acid, sodium hydroxide, potassium hydroxide and the like.

Examples of the antioxidant include dibutylhydroxytoluene (BHT), butylhydroxyanisole (BHA), dl-α-tocopherol, erythorbic acid and the like. Examples of the antiseptic and preservative include paraben (methylparaben etc.), benzyl alcohol, sodium dehydroacetate, sorbic acid and the like.

Examples of the corrigent include ascorbic acid, erythritol, sodium L-glutamate and the like. Examples of the sweetener include aspartame, licorice extract, saccharin and the like. Examples of the flavor include l-menthol, d-camphor, vanillin and the like. Examples of the colorant include tar pigment (Food Color Red No. 2, Food Color Blue No. 1, Food Color yellow No. 4 etc.), inorganic pigment (red iron oxide, yellow iron oxide, black iron oxide etc.), natural dye (turmeric extract, β-carotene, sodium copper-chlorophyllin etc.) and the like.

While the blood pH increasing agent of the present invention can be administered to or ingested by a subject by a general administration route such as oral administration, administration into blood, rectal administration and the like, oral administration (oral ingestion) is preferable.

The daily intake amount or dose of the blood pH increasing agent of the present invention is appropriately determined according to the sex, age of the subject of application (hereinafter to be also referred to as "application subject" in the present specification), the condition and the degree thereof observed in the application subject, the form of the blood pH increasing agent of the present invention, the administration method thereof, and the like. When the application subject is a human adult, it is generally 0.01 g/kg of body weight to 0.15 g/kg of body weight, preferably 0.02 g/kg of body weight to 0.15 g/kg of body weight, more preferably 0.1 g/kg of body weight to 0.15 g/kg of body weight, as the total amount of aspartic acid (total amount converted to free form). The above-mentioned amount may be ingested or administered at one time, or may be ingested or administered in several portions (2 to 4 portions) per day.

The blood pH increasing agent of the present invention can be used for therapeutic or non-therapeutic purposes. For therapeutic use, the blood pH increasing agent of the present invention is applied to a subject affected with a disease with a decrease in blood pH. For non-therapeutic use, the blood pH increasing agent of the present invention is applied to a subject who is healthy but expected to have a temporary decrease in blood pH due to intense exercise or undernutrition, and the like, or a subject whose blood pH has actually dropped temporarily due to intense exercise or undernutrition, and the like. The timing of the administration (ingestion) of the blood pH increasing agent of the present invention for non-therapeutic use is not particularly limited as long as a desired effect is obtained, and it is generally preferably before or during performing exercise. When it is before performing exercise, it can be unlimitatively administered to (ingested by) the subject immediately before to 3 hr before, preferably, immediately before to 2 hr before, particularly preferably, immediately before to 1 hr before, performing exercise.

3. Food and Drink

The present invention also provides a food or drink containing the intermittent endurance capacity improving agent of the present invention and/or the blood pH increasing agent of the present invention (hereinafter sometimes to be referred to as "the food or drink of the present invention").

The food or drink of the present invention can be prepared by mixing the aforementioned intermittent endurance capacity improving agent and/or blood pH increasing agent of the present invention with the existing food or drink. Therefore, the food or drink of the present invention can also afford an intermittent endurance capacity improving effect and/or blood pH increasing effect when ingested.

The food or drink of the present invention is not particularly limited as long as it can contain the intermittent endurance capacity improving agent and/or blood pH increasing agent of the present invention, and can afford a desired effect. For example, it is preferably processed into a food or drink that is easy to ingest before and during exercise, such as powder, granule, tablet, soft drink, jelly-like composition, or the like.

In the food or drink of the present invention, a food in a unit package form per meal when aspartic acid (or a salt thereof) alone is mixed as the active ingredient contains 0.1 to 6 g (preferably, 0.5 to 5 g, more preferably 1 to 5 g, further preferably 2 to 5 g, particularly preferably 3 to 5 g) of aspartic acid per meal. When aspartic acid (or a salt thereof) and tyrosine (or a salt thereof) are contained as the active ingredients, 0.1 to 3 g of aspartic acid and 0.1 to 3 g of tyrosine (preferably, 0.5 to 3 g of aspartic acid and 0.5 to 3 g of tyrosine, more preferably 1 to 3 g of aspartic acid and 1 to 3 g of tyrosine, particularly preferably 1.5 to 2.5 g of aspartic acid and 1.5 to 2.5 g of tyrosine) are contained per meal. In the food or drink of the present invention, a food or drink with which the intermittent endurance capacity improving agent and/or blood pH increasing agent of the present invention are/is mixed is more preferably a food or drink consisting only of starting materials that are substantially free of aspartic acid and/or tyrosine (or components that can produce these amino acids in and/or in the body by hydrolysis, metabolism, and the like). Using such food or drink as a starting material, the amount(s) of aspartic acid and/or tyrosine in the food or drink of the present invention can be accurately determined based on the amount(s) of the intermittent endurance capacity improving agent and/or blood pH increasing agent of the present invention. As a result, appropriate and safe amount(s) of aspartic acid and/or tyrosine can be easily ingested.

The food or drink in a "unit package form per meal" is a food with a predetermined amount to be ingested per meal. In the present specification, the food or drink is a concept widely encompassing something that can be ingested orally (excluding pharmaceutical products), and includes not only what is called "food" but also drink, health aid food, food with health claims, supplement and the like. Examples of the unit package form per meal include a form that defines a given amount in a pack, package, bottle etc. in the case of drink, candy, chewing gum, jelly, and the like, and package and the like can define a given amount in the case of granular, powdery and slurry foods. Alternatively, a form such as a container and the like indicating the intake amount per meal can be mentioned.

Other features of the invention will become apparent in the course of the following descriptions of exemplary embodiments which are given for illustration of the invention and are not intended to be limiting thereof.

EXAMPLES

Experimental Example 1. Screening for Substance Capable of Improving Intermittent Endurance Capacity After ingesting a test substance into 6-week-old C57BL/6J male mice, a mouse YO-YO test was conducted to evaluate an intermittent endurance capacity improving effect of the test substance using the intermittent endurance capacity of each individual as an index. As the test substance, 20 kinds of amino acids (or salts thereof) were used. These were administered alone or administered in various combinations, and which amino acid or a combination thereof had an intermittent endurance capacity improving effect was examined. Furthermore, the combined use of amino acid and caffeine or carbohydrate, and the relationship between the amounts thereof used and the like were also comprehensively examined from the viewpoint of the intermittent endurance capacity improving effect.

Preliminary Running and Grouping

Preliminary running was performed on the mice one week before the main test. The inclination of the treadmill was 20 degrees, one set included walking for 30 sec (speed 5 m/min) and running for 2 min, and the running speed was gradually increased to 12 to 33 m/min as the number of the sets increased. Unable to run was judged when the mouse could not keep up with the running speed. When the state of unable to run was observed in two sets in succession, the mouse was determined to have dropped out of the present evaluation system, and the number of sets run by each individual up to that time point was used as the intermittent endurance ability of the individual. Grouping was performed such that the number of running sets and body weight of each individual obtained in the preliminary running were about the same for each group.

Main Test

In the week following the preliminary running, the mice evaluated for the intermittent endurance capacity were orally administered with an aqueous solution containing a test substance in a dose of 1 to 2 g/kg mouse body weight, or water (negative control) at 20 mL/kg mouse body weight. Caffeine, which is known to have an intermittent endurance capacity improving effect, was used as a positive control in this test. From 30 min after the oral administration, the above-mentioned YO-YO test was performed to evaluate the effect of the test substance on the number of runnable sets of each individual. The evaluation of whether intermittent endurance capacity has improved was performed by subtracting the number of runnable sets during preliminary running from the number of runnable sets confirmed when the test substance was ingested, and calculating an increase in the number of runnable sets by the ingestion of the test substance.

Figure 1:
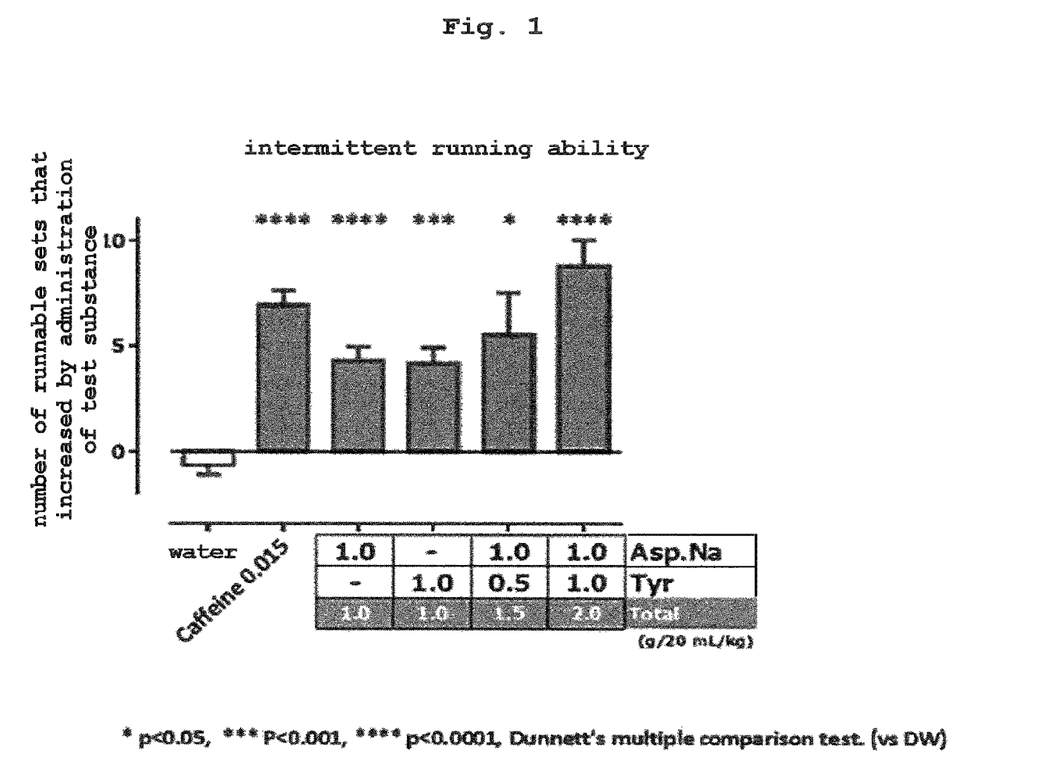
FIG. 1 shows improved intermittent endurance capacity of mice that ingested the intermittent endurance capacity improving agent of the present invention.

The results are shown in FIG. 1. Single administration of aspartic acid or tyrosine significantly increased the number of runnable sets as compared to the administration of water (negative control). It was shown that the combined use of aspartic acid and tyrosine afforded a still higher effect than the single administration of aspartic acid or tyrosine. It was also found that when aspartic acid and tyrosine are used in combination, a more preferable effect is obtained by setting the administration ratio thereof to near 1:1. On the other hand, single or combined administration of amino acid other than aspartic acid and tyrosine did not show a significant intermittent endurance capacity improving effect (data not shown).

Experimental Example 2. Increase in Mouse Plasma pH by Oral Administration of Aspartic Acid Using 7- to 9-week-old C57BL/6J male mice, aspartic acid at the dose of 1 g/kg, or sodium hydrogen carbonate (positive control) was orally administered. After 30 min, 60 min, 120 min from the oral administration, blood samples were collected under isoflurane anesthesia. The obtained blood was centrifuged, the plasma was collected, and blood pH was measured using i-STAT (manufactured by abbott).

Figure 2:
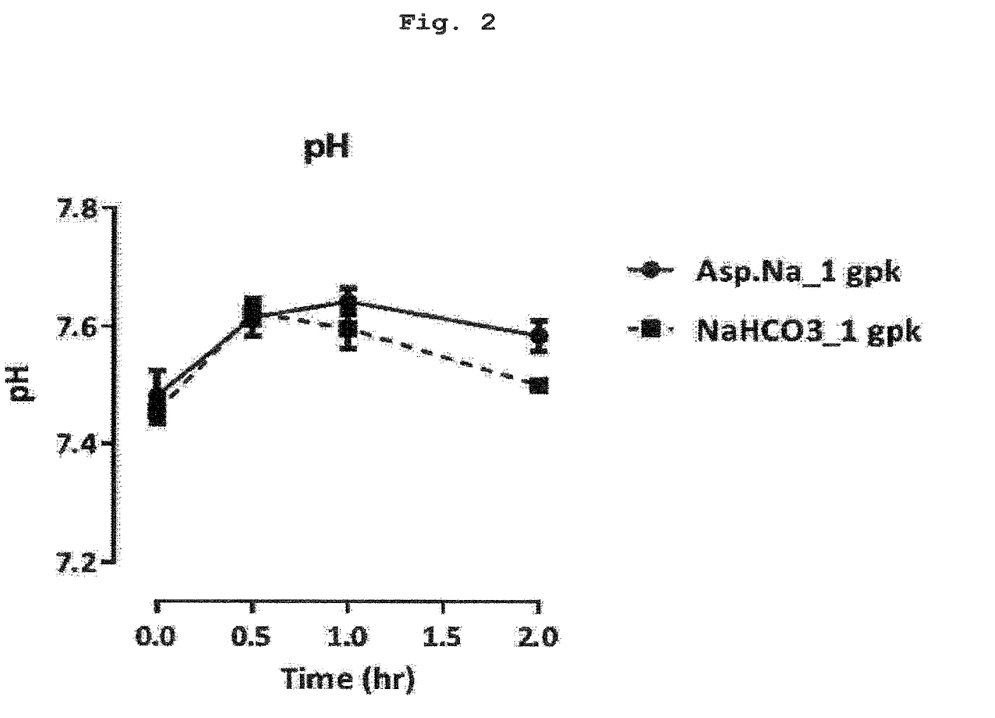
FIG. 2 shows time-course changes in the plasma pH of mice that ingested the blood pH increasing agent of the present invention.
Figure 3:
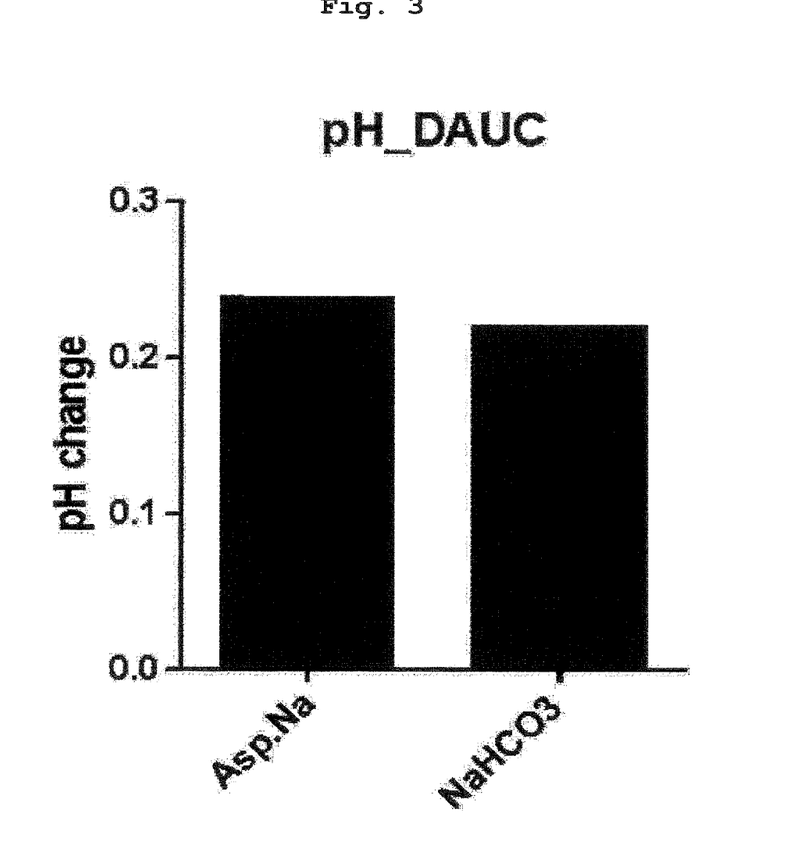
FIG. 3 shows variation in plasma pH of mice that ingested the blood pH increasing agent of the present invention, as area under the curve.

The results are shown in FIGS. 2 and 3. FIG. 2 shows time-course changes in the plasma pH of mouse after administration of aspartic acid. FIG. 3 shows area under the curve in the graph of plasma pH shown in FIG. 2. As shown in the both Figures, it was confirmed that aspartic acid affords an effect of increasing blood pH even after 0.5 hr to 2 hr from the administration. On the other hand, sodium hydrogen carbonate used as the positive control reached peak at 0.5 hr, and the pH increasing effect disappeared rapidly thereafter.

Industrial Applicability

The present invention can improve intermittent endurance capacity of players for game sports such as soccer, basketball and the like. Also, the present invention can improve the performance of athletes by increasing blood pH. Furthermore, the present invention can treat, improve, and/or prevent subjects affected with diseases associated with a decrease in blood pH such as gout and the like. Therefore, the present invention is extremely useful in the production field of sports supplements and pharmaceutical products.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for improving intermittent endurance capacity, comprising administering an effective amount of aspartic acid to a subject in need thereof,
    wherein a timing of the administering is immediately before to 3 hours before or during performing intermittent exercise,
    wherein the administering of the aspartic acid is a single administration, wherein the single administration improves intermittent endurance capacity in the subject.

2. The method according to claim 1, further comprising administering tyrosine to the subject.

3. The method according to claim 2, wherein said aspartic acid and said tyrosine are administered in an aspartic acid:tyrosine weight ratio of 1:0.1 to 10.

4. The method according to claim 1, wherein said aspartic acid is administered in the form of a food or drink.

5. The method according to claim 2, wherein said aspartic acid and said tyrosine are administered in the form of a food or drink.

6. The method according to claim 1, wherein the timing of the administering is immediately before to 3 hours before performing intermittent exercise.

7. The method according to claim 1, wherein the timing of the administering is during performing intermittent exercise.

* * * * *